(12) United States Patent
Novak et al.

(10) Patent No.: US 8,117,906 B2
(45) Date of Patent: Feb. 21, 2012

(54) GAS SENSOR SHIELD WITHOUT PERFORATIONS

(75) Inventors: Robert F. Novak, Farmington Hills, MI (US); Richard E. Soltis, Saline, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 12/774,541

(22) Filed: May 5, 2010

(65) Prior Publication Data

US 2011/0131953 A1 Jun. 9, 2011

(51) Int. Cl.
*G01M 15/10* (2006.01)
(52) U.S. Cl. .................... 73/114.71; 73/23.31
(58) Field of Classification Search .............. 73/23.31, 73/114.71
See application file for complete search history.

(56) References Cited

U.S. PATENT DOCUMENTS

| | | | |
|---|---|---|---|
| 4,228,128 A | 10/1980 | Esper et al. | |
| 4,323,440 A | 4/1982 | Akatsuka | |
| 4,784,728 A * | 11/1988 | Capone | 205/785 |
| 5,329,806 A | 7/1994 | McClanahan et al. | |
| 5,547,552 A | 8/1996 | Hasegawa et al. | |
| 5,781,878 A * | 7/1998 | Mizoguchi et al. | 701/109 |
| 5,785,829 A * | 7/1998 | Watanabe | 204/427 |
| 5,886,248 A * | 3/1999 | Paulus et al. | 73/23.31 |
| 6,303,012 B1 | 10/2001 | Inoue et al. | |
| 6,551,498 B2 * | 4/2003 | Nelson | 205/784.5 |
| 6,554,984 B2 | 4/2003 | Inoue et al. | |
| 6,843,105 B1 * | 1/2005 | France | 73/31.05 |
| 6,849,238 B2 * | 2/2005 | Weyl et al. | 422/94 |
| 7,197,912 B1 * | 4/2007 | Duce et al. | 73/31.05 |
| 7,281,368 B2 * | 10/2007 | Miyake et al. | 60/285 |
| 7,310,991 B2 * | 12/2007 | Lange et al. | 73/23.31 |
| 7,406,854 B2 * | 8/2008 | Lange et al. | 73/1.06 |
| 2002/0134692 A1 * | 9/2002 | Nelson | 205/784 |
| 2007/0214862 A1 | 9/2007 | Kubinski et al. | |
| 2009/0108096 A1 * | 4/2009 | Stephan et al. | 239/135 |

* cited by examiner

*Primary Examiner* — Freddie Kirland, III
(74) *Attorney, Agent, or Firm* — Allan J. Lippa; Alleman Hall McCoy Russell & Tuttle LLP

(57) ABSTRACT

Various embodiments of a heated gas sensor with a porous metal shield without perforations are disclosed. In one example, the gas sensor is used in an intake manifold of an engine. In another embodiment, the gas sensor is used in an exhaust passage of an engine. The porous metal shield without perforations allows gas to permeate the shield for measurement while retarding flame propagation if gases ignite in the vicinity of a sensing element of the heated gas sensor.

16 Claims, 3 Drawing Sheets

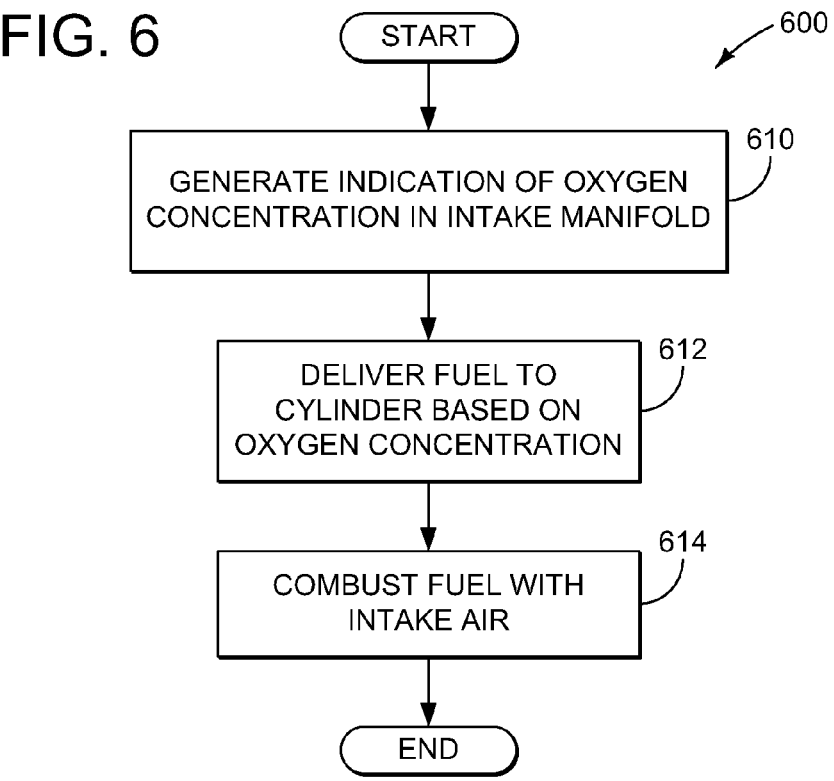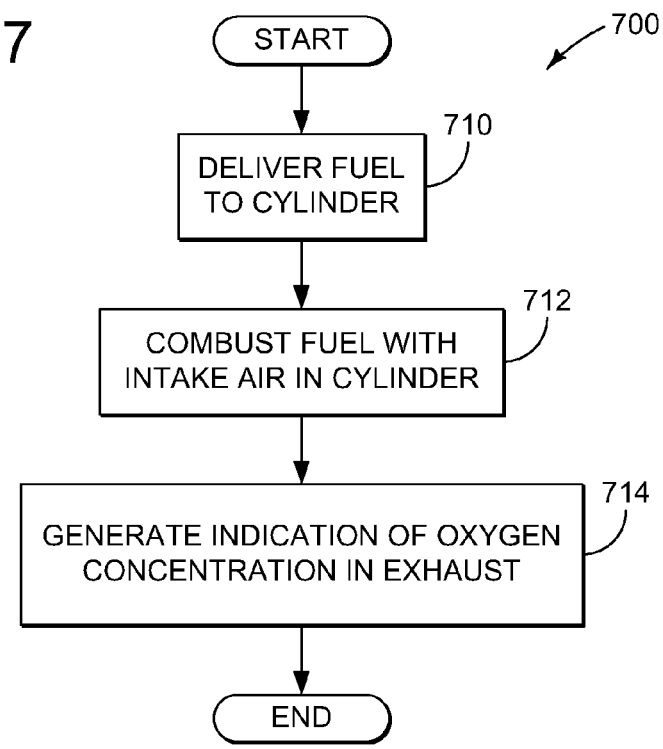

US 8,117,906 B2

GAS SENSOR SHIELD WITHOUT PERFORATIONS

TECHNICAL FIELD

The present application relates generally to a gas sensor for sensing a gas concentration in a gas flow through an engine in a vehicle, and more particularly to a shield of the gas sensor.

BACKGROUND AND SUMMARY

Gas sensors can be used for measuring a concentration of a gas (e.g., oxygen, carbon dioxide) in a gas flow through an engine in a vehicle. For example, a gas sensor may be positioned in an intake manifold of the engine for measuring gases that are entering a combustion chamber and/or in an exhaust passage of the engine for measuring gases that are contained in exhaust leaving the combustion chamber. Such gas sensors located in the intake manifold or exhaust passage can be utilized for determining an accurate air-fuel ratio, for example, and engine operating parameters (e.g., sparking timing, fuel injection, etc.) may be adjusted accordingly thereby improving or maintaining engine performance.

In order to protect a sensing element of the sensor from debris such as soot, a sensing element of the sensor may be covered by a shield that is perforated so that the gas flow may reach the sensing element. Further, in some examples, the gas sensors may be operated at high temperatures (e.g., 700-800° C.). When the gas sensor is positioned in certain locations, fuel vapors may pass through the sensor shield and interact with heating elements of the sensor to ignite. The ignited constituents may then interact with other gasses or substances in the vicinity of the sensor, thereby degrading engine operation.

The inventors herein have recognized the above issues and have devised an approach to at least partially address them. In one example, a method for an engine in a vehicle is disclosed. The method comprises delivering a fuel to a cylinder of the engine, combusting the fuel with a gas flow through the cylinder that enters the cylinder from an intake manifold and leaves the cylinder through an exhaust passage, and generating an indication of oxygen concentration in the gas flow via a heated gas sensor, the gas sensor having a porous metal shield without perforations.

In one embodiment, the fuel may be gasoline and the gas sensor may be positioned in the intake manifold of the engine. Due to a high operating temperature of the sensor, fuel vapor in the intake manifold may ignite in the vicinity of a sensing element of the sensor. By using a porous metal shield without perforations to cover the sensing element, the gas flow in the intake manifold can still permeate the shield so that an indication of gas concentration can be generated and, if fuel vapor in the gas flow is ignited in the vicinity of the sensing element, flame propagation can be retarded by the shield and contained to within the shield.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 6 shows a flow chart illustrating a routine for an engine with a gas sensor positioned in an intake manifold.
FIG. 7 shows a flow chart illustrating a routine for an engine with a gas sensor positioned in an exhaust passage.

DETAILED DESCRIPTION

Figure 1:
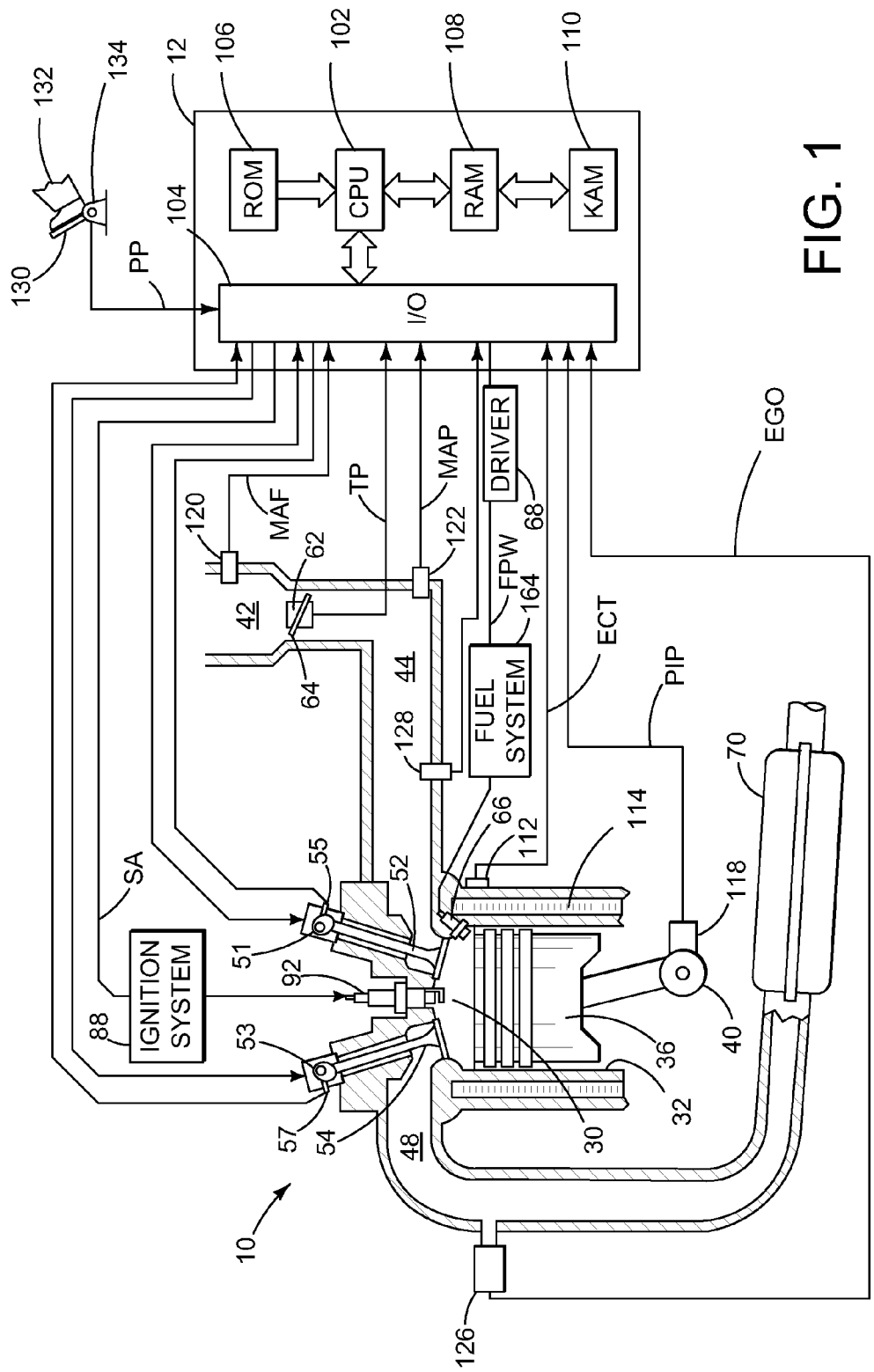
FIG. 1 shows a schematic diagram of an engine.

The following description relates to embodiments of a shield for a heated gas sensor that generates an indication of a gas concentration in a gas flow through an engine in a vehicle. In one embodiment, the gas sensor is located in an intake manifold of the engine for detecting oxygen concentration of the intake air. In another embodiment, the gas sensor is located in an exhaust passage of the engine for detecting oxygen concentration of the exhaust from the engine. FIG. 1 shows a schematic diagram of an engine including a gas sensor in the intake manifold and an exhaust sensor in the exhaust passage. FIGS. 2-5 show examples of a gas sensor and a shield for covering a sensing element of the gas sensor. FIGS. 6 and 7 show flow charts illustrating control routines for an engine with a gas sensor in the intake manifold and the exhaust passage, respectively.

FIG. 1 is a schematic diagram showing one cylinder of multi-cylinder engine 10, which may be included in a propulsion system of an automobile. Engine 10 may be controlled at least partially by a control system including controller 12 and by input from a vehicle operator 132 via an input device 130. In this example, input device 130 includes an accelerator pedal and a pedal position sensor 134 for generating a proportional pedal position signal PP. Combustion chamber (i.e., cylinder) 30 of engine 10 may include combustion chamber walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of a vehicle via an intermediate transmission system. Further, a starter motor may be coupled to crankshaft 40 via a flywheel to enable a starting operation of engine 10.

Combustion chamber 30 may receive intake air from intake manifold 44 via intake passage 42 and may exhaust combustion gases via exhaust passage 48. Intake manifold 44 and exhaust passage 48 can selectively communicate with combustion chamber 30 via respective intake valve 52 and exhaust valve 54. In some embodiments, combustion chamber 30 may include two or more intake valves and/or two or more exhaust valves.

In this example, intake valve 52 and exhaust valves 54 may be controlled by cam actuation via respective cam actuation systems 51 and 53. Cam actuation systems 51 and 53 may each include one or more cams and may utilize one or more of cam profile switching (CPS), variable cam timing (VCT), variable valve timing (VVT) and/or variable valve lift (VVL) systems that may be operated by controller 12 to vary valve operation. The position of intake valve 52 and exhaust valve 54 may be determined by position sensors 55 and 57, respectively. In alternative embodiments, intake valve 52 and/or exhaust valve 54 may be controlled by electric valve actuation. For example, cylinder 30 may alternatively include an intake valve controlled via electric valve actuation and an exhaust valve controlled via cam actuation including CPS and/or VCT systems.

Fuel injector 66 is shown coupled directly to combustion chamber 30 for injecting fuel directly therein in proportion to the pulse width of signal FPW received from controller 12 via electronic driver 68. In this manner, fuel injector 66 provides what is known as direct injection of fuel into combustion chamber 30. The fuel injector may be mounted in the side of the combustion chamber or in the top of the combustion chamber, for example. Fuel may be delivered to fuel injector 66 by a fuel system 164 including a fuel tank, a fuel pump, and a fuel rail. In some embodiments, combustion chamber 30 may alternatively or additionally include a fuel injector arranged in intake manifold 44 in a configuration that provides what is known as port injection of fuel into the intake port upstream of combustion chamber 30. Further, in some embodiments, the fuel injected to combustion chamber 30 may be gasoline, for example. In other embodiments, the fuel injected to combustion chamber 30 may be hydrogen.

Intake passage 42 may include a throttle 62 having a throttle plate 64. In this particular example, the position of throttle plate 64 may be varied by controller 12 via a signal provided to an electric motor or actuator included with throttle 62, a configuration that is commonly referred to as electronic throttle control (ETC). In this manner, throttle 62 may be operated to vary the intake air provided to combustion chamber 30 among other engine cylinders. The position of throttle plate 64 may be provided to controller 12 by throttle position signal TP. Intake passage 42 may include a mass air flow sensor 120 and a manifold air pressure sensor 122 for providing respective signals MAF and MAP to controller 12.

Ignition system 88 can provide an ignition spark to combustion chamber 30 via spark plug 92 in response to spark advance signal SA from controller 12, under select operating modes. Though spark ignition components are shown, in some embodiments, combustion chamber 30 or one or more other combustion chambers of engine 10 may be operated in a compression ignition mode, with or without an ignition spark.

Exhaust gas sensor 126 is shown coupled to exhaust passage 48 upstream of emission control device 70. Sensor 126 may be any suitable sensor for providing an indication of exhaust gas air-fuel ratio such as a linear oxygen sensor or UEGO (universal or wide-range exhaust gas oxygen), a two-state oxygen sensor or EGO, a HEGO (heated EGO), a $NO_x$, HC, or CO sensor. Emission control device 70 is shown arranged along exhaust passage 48 downstream of exhaust gas sensor 126. Device 70 may be a three way catalyst (TWC), NO trap, various other emission control devices, or combinations thereof. In some embodiments, during operation of engine 10, emission control device 70 may be periodically reset by operating at least one cylinder of the engine within a particular air/fuel ratio.

Further, in addition to sensor 126, exhaust gas sensor 128 may be coupled to intake manifold 44 as shown in FIG. 1. Sensor 128 may be any suitable sensor for providing an indication of oxygen concentration in the intake manifold, such as a linear oxygen sensor, a two-state oxygen sensor, etc. For example, sensor 128 may provide an indication of oxygen concentration in order to determine an accurate air-fuel ratio for combustion in the cylinders of the engine.

Controller 12 is shown in FIG. 1 as a microcomputer, including microprocessor unit 102, input/output ports 104, an electronic storage medium for executable programs and calibration values shown as read only memory chip 106 in this particular example, random access memory 108, keep alive memory 110, and a data bus. Controller 12 may receive various signals from sensors coupled to engine 10, in addition to those signals previously discussed, including measurement of inducted mass air flow (MAF) from mass air flow sensor 120; engine coolant temperature (ECT) from temperature sensor 112 coupled to cooling sleeve 114; a profile ignition pickup signal (PIP) from Hall effect sensor 118 (or other type) coupled to crankshaft 40; throttle position (TP) from a throttle position sensor; and absolute manifold pressure signal, MAP, from sensor 122. Engine speed signal, RPM, may be generated by controller 12 from signal PIP. Manifold pressure signal MAP from a manifold pressure sensor may be used to provide an indication of vacuum, or pressure, in the intake manifold. Note that various combinations of the above sensors may be used, such as a MAF sensor without a MAP sensor, or vice versa. During stoichiometric operation, the MAP sensor can give an indication of engine torque. Further, this sensor, along with the detected engine speed, can provide an estimate of charge (including air) inducted into the cylinder. In one example, sensor 118, which is also used as an engine speed sensor, may produce a predetermined number of equally spaced pulses every revolution of the crankshaft.

Storage medium read-only memory 106 can be programmed with computer readable data representing instructions executable by processor 102 for performing the methods described below as well as other variants that are anticipated but not specifically listed.

As described above, FIG. 1 shows only one cylinder of a multi-cylinder engine, and each cylinder may similarly include its own set of intake/exhaust valves, fuel injector, spark plug, etc.

Figure 2:
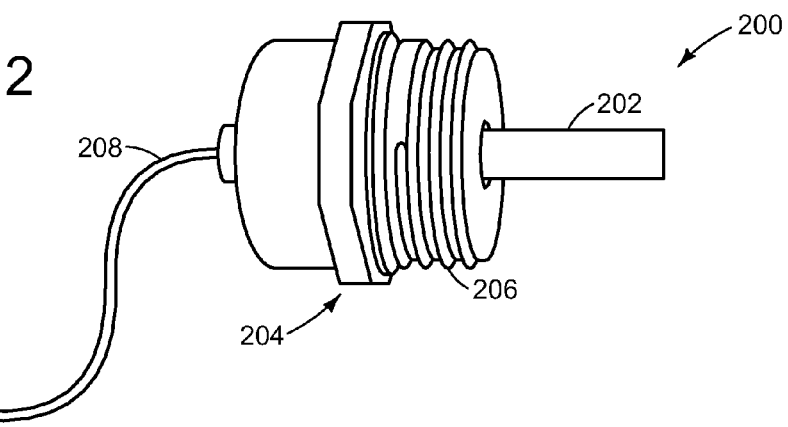
FIG. 2 shows a schematic diagram of a gas sensor without a shield.

Continuing to FIG. 2, a gas sensor 200 without a shield is shown. Gas sensor 200 may be positioned in an exhaust system such as sensor 126 in FIG. 1 or positioned in an intake manifold such as sensor 128 in FIG. 1, for example. Sensor 200 may be any suitable sensor for providing an indication of a gas concentration, such as oxygen, in an intake manifold or an exhaust passage, as described above with reference to FIG. 1. For example, sensor 200 may be a linear oxygen sensor, an EGO sensor, etc. Further, sensor 200 may be a heated sensor.

As shown in FIG. 2, sensor 200 includes a body portion 204 with a threaded portion 206 for engagement with a suitably threaded aperture in an intake manifold or exhaust passage of an engine. Body portion 204 may be made of steel, for example. Further, cord 208 extends from body portion 204. Cord 208 contains wires (not shown) for electrical connection to a control unit that enable sensor 200 to be used in a feedback fuel control system, for example.

Sensor 200 further includes sensing element 202 which extends outwardly from body portion 204 in the opposite direction as cord 208, as shown in FIG. 2. When installed such as in the example of FIG. 1, sensing element 202 extends into the intake manifold or exhaust passage past a wall (e.g., inner surface) of the intake manifold or exhaust passage.

Sensing element 202 may be responsive to the partial pressure of oxygen in the gas flow through an engine and may be made of a ceramic metal oxide such as a zirconium oxide based material, for example. Further, sensing element 202 may include a heating element for heating the sensor in order to lower the impedance of the metal oxide and minimize deposits which may degrade the sensor while the sensor is in operation, for example. As an example, sensor 200 may have an operating temperature between 700 and 850° C.

Figure 3A:
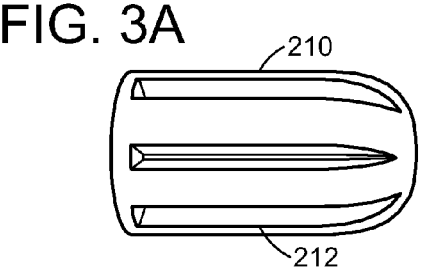
FIGS. 3A and 3B show examples of shields for a gas sensor.

In order to protect sensing element 202 from debris which may be contained in the intake air or exhaust gas, such as soot, sensing element may be covered by a shield. FIG. 3A shows an example embodiment of a shield 210 which includes several perforations 212 to allow exhaust gas to reach the sensing element for gas measurement. The perforations in FIG. 3A are depicted as through-openings in the shape of slits along the length of the shield, however, perforations in the shield may be various sizes and/or shapes and may vary in number. When such a shield with perforations is utilized to cover the sensing element, ignition of fuel vapors that are present in the intake manifold or hydrogen present in the exhaust passage via interaction with the heated sensing element may escape through the shield via one or more of the perforations.

Figure 3B:
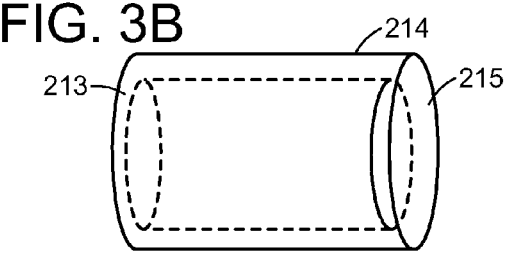

In contrast to the shield shown in FIG. 3A, FIG. 3B shows an example embodiment of a shield 214 for a gas sensor that is not perforated and thus has no through-openings exposing the heating elements to gasses in the corresponding passage in which the sensor is installed, and shield 214 may be an insulating shield. Shield 214 may be made of a sintered metal material, for example. Further, the metal may be porous such that a gas flow may permeate the shield and the gas sensor can generate an indication of concentration of a desired constituent of the gas flow. The size of the pores may depend on various parameters such as the type of metal of the shield, the temperature at which the sensor operates, and the location of the sensor, for example.

Figure 4:
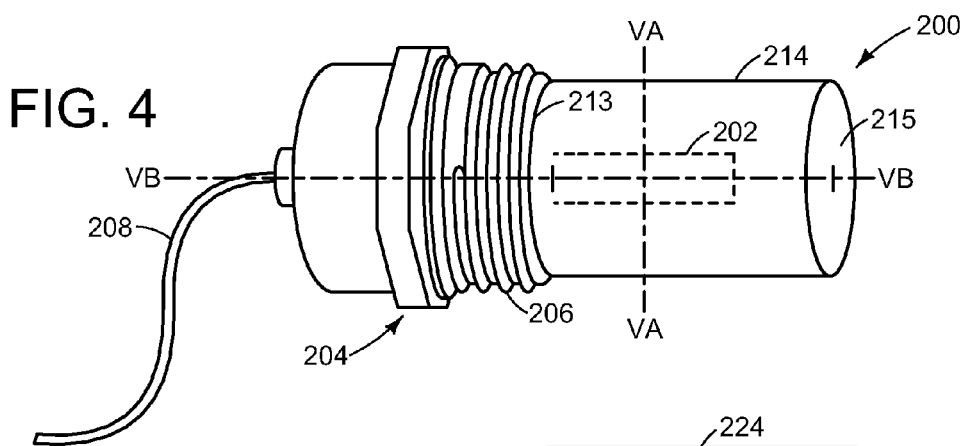
FIG. 4 shows a schematic diagram of a gas sensor with a shield without perforations.

As shown in FIG. 3B, shield 214 has a cylindrical shape with one closed end 215 and one open end 213 which seals against the body portion (204) of the sensor, as shown in FIG. 4. As such, when the shield is installed to cover sensing element 202, the open end of the shield may be flush with the inner surface of the intake manifold or exhaust passage if the body portion of the gas sensor is flush with the inner surface, or the open end of the shield may be positioned away from (e.g., a few millimeters) the inner surface of the intake manifold or exhaust passage if the body portion of the gas sensor extends into the intake manifold or exhaust passage.

Further, in some embodiments, if the gas sensor is used in an environment in which liquid water may be present, a waterproof membrane that is permeable to gases (e.g., Gore-Tex® membrane) may be placed over the porous metal shield. Further still, in other embodiments, shield 214 may be placed over an existing perforated shield.

FIG. 4 shows shield 214 of FIG. 3B covering sensing element 202 such that open end 213 is in contact with body portion 204 of gas sensor 200. In such a configuration, sensing element 202 is completely enclosed and any ignition of gases in the presence of sensing element 202 internal to the shield may be extinguished without causing ignition outside of the shield since shield 214 is not perforated.

Figure 5A:
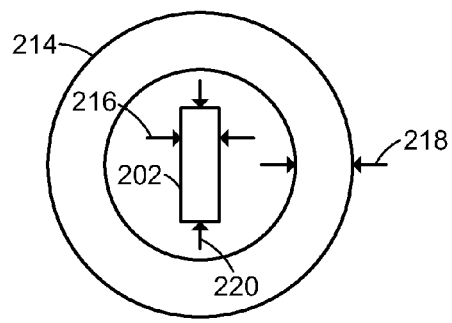
FIGS. 5A and 5B show cross-sectional views of a gas sensor shield without perforations taken along lines VA and VB of FIG. 4, respectively.

FIGS. 5A and 5A show cross-sectional views of shield 214, which does not have perforations, and sensing element 202 when shield 214 is installed on sensor 200 to cover sensing element 202.

FIG. 5A shows a cross-section of shield 214 and sensing element 202 taken along line VA of FIG. 4, through the axial direction of the cylinder and along the radial direction. As shown, shield 214 has a thickness indicated at 218. Like the porosity of the shield, the thickness of shield 214 may depend on various parameters such as operating temperature of the sensor, location of the sensor, etc. Further, as shown, the length (indicated at 220) and the width (indicated at 216) of sensing element 202 are less than the diameter of the inner surface of shield 214. Thus, the inner cross-sectional area of shield 214 is greater than the cross-sectional area of sensing element 202 and shield 214 does not come in contact with sensing element 202.

Figure 5B:
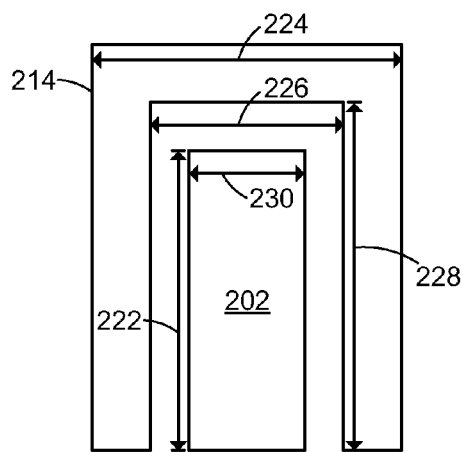

FIG. 5B shows a cross-section of shield 214 and sensing element 202 taken along line VB of FIG. 4, through the radial direction of the cylinder and along the axial direction at the point where the outer diameter of shield 214 is a maximum. As shown, shield 214 has an outer diameter indicated at 224 and an inner diameter indicated at 226. The width (indicated at 230) of sensing element 202 is less than the inner diameter 226 of shield 214. Further, the inner length (indicated at 228) of shield 214 is greater than the length (indicated at 222) of sensing element 202 that extends past the body portion of the sensor. As such, when installed on a gas sensor to cover sensing element 202, shield 214 does not come in contact with sensing element 202 and shield 214 does not interfere with measurements taken by the sensor.

Continuing to FIGS. 6 and 7, flowcharts illustrating routines in which a sensor such as sensor 200 described above is used are shown.

FIG. 6 shows a flowchart illustrating a routine 600 in which a heated oxygen sensor with a porous metal shield such as shield 214 of FIGS. 3B-5B is used in an intake manifold of the engine. Specifically, routine 600 controls combustion in the cylinders of an engine based at least in part on an indication of oxygen concentration measured in the intake manifold.

At 610 of routine 600, an indication of oxygen concentration in the intake manifold is generated by an oxygen sensor with a porous metal shield, such as the porous metal shield described above. Once the oxygen concentration is determined, routine 600 proceeds to 612 where fuel is delivered to the cylinders of the engine and the amount of fuel delivered is based on the oxygen concentration detected at 610. Finally, at 614, the fuel is combusted with intake air in the cylinders of the engine.

In such an example, the engine may be fueled with gasoline and fuel vapors may be present in the intake manifold. As such, fuel vapors may enter the intake manifold where they may ignite in the vicinity of the heated gas sensor. When a porous metal shield is used to cover the sensing element, flame propagation may be retarded and flames do not pass completely through the shield.

In the example of FIG. 7, a flow chart illustrating a routine 700 in which a heated oxygen sensor with a porous metal shield such as shield 214 of FIGS. 3B-5B is used in an exhaust passage of the engine. Specifically, routine 700 controls combustion in an engine in which an exhaust gas sensor is used to determine an air-fuel ratio of the exhaust, for example.

At 710 of routine 700, fuel is delivered to the cylinder. Next, at 712, fuel is combusted with intake air in the cylinder. Finally, an indication of oxygen concentration in the exhaust is generated at 714.

In such an example, the engine may be fueled with hydrogen, for example. As such, hydrogen may leave the cylinders of the engine in the exhaust gas. In the presence of the heated sensing element of the gas sensor, oxygen and hydrogen may ignite. If a porous metal shield, as described above, covers and encloses the sensing element of the sensor, flame propagation may be retarded and may be extinguished by the shield.

As another example, the shield may be used to reduce flame propagation in a hydrogen fuel cell vehicle in which hydrogen may be present in the exhaust.

Thus, a porous metal shield without perforations may be used to cover and protect a heated gas sensor that may be used in an intake manifold and/or an exhaust passage of an engine. As described above, the shield may retard flame propagation when gases in the presence of a heated sensor ignite while still allowing gas to permeate the shield so that measurement of a desired gas constituent may be accurately carried out.

Note that the example control and estimation routines included herein can be used with various engine and/or vehicle system configurations. The specific routines described herein may represent one or more of any number of processing strategies such as event-driven, interrupt-driven, multi-tasking, multi-threading, and the like. As such, various acts, operations, or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated acts or functions may be repeatedly performed depending on the particular strategy being used. Further, the described acts may graphically represent code to be programmed into the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and nonobvious combinations and subcombinations of the various systems and configurations, and other features, functions, and/or properties disclosed herein.

The following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application.

Such claims, whether broader, narrower, equal, or different in scope to the original claims, also are regarded as included within the subject matter of the present disclosure.

The invention claimed is:

1. A method for a vehicle engine, comprising:
   delivering a fuel to a cylinder of the engine;
   combusting the fuel with a gas flow through the cylinder that: enters the cylinder from an intake manifold in which fuel vapors are present, and leaves the cylinder through an exhaust passage; and
   generating an indication of oxygen concentration in the gas flow in the intake manifold via a heated gas sensor having a porous metal shield without perforations;
   wherein the porous metal shield retards flame propagation when fuel vapors in the presence of the heated gas sensor are ignited.

2. The method of claim 1, further comprising generating the indication when an operating temperature of the gas sensor is between 700 and 850° C.

3. The method of claim 1, wherein the fuel is gasoline.

4. The method of claim 3, wherein an amount of fuel delivered to the engine is based on the indication of oxygen concentration generated by the gas sensor in the intake manifold.

5. The method of claim 1 further comprising igniting the fuel vapors in the intake manifold gas flow in a vicinity of a sensing element of the heated gas sensor, retarding flame propagation of the ignition by the shield, and retaining the flame propagation within the shield.

6. An intake gas sensor, comprising:
   a heated sensing element for detecting a gas concentration in an intake manifold of an engine where fuel vapors are present, the heated sensing element extending outwardly from a body portion of the gas sensor; and
   a cylindrical, porous metal shield without perforations which covers the sensing element, the shield having one closed end and one open end, the open end being in contact with the body portion of the gas sensor, and the shield configured to retard flame propagation;
   wherein the porous metal shield retards flame propagation when fuel vapors in the presence of the heated sensing element are ignited.

7. The gas sensor of claim 6, wherein an operating temperature of the gas sensor is between 700 and 850° C.

8. The gas sensor of claim 6, wherein the porous metal shield is a sintered metal shield.

9. The gas sensor of claim 6, wherein an inner cross-sectional area of the porous metal shield is greater than a cross-sectional area of the sensing element such that the porous metal shield does not come in contact with the sensing element.

10. The gas sensor of claim 6, wherein an inner length of the porous metal shield is greater than a length of the sensing element that extends past the body portion of the gas sensor such that the porous metal shield does not come in contact with the sensing element.

11. The gas sensor of claim 6, wherein the porous metal shield is an insulating shield.

12. A method for a vehicle engine, comprising:
   delivering a fuel to a cylinder of the engine via a direct cylinder injector positioned in the cylinder;
   combusting the fuel with a gas flow through the cylinder that: enters the cylinder from an intake manifold in which fuel vapors are present, and leaves the cylinder through an exhaust passage;
   generating a measurement of oxygen concentration in the gas flow in the intake manifold via a heated gas sensor having a cylindrical porous metal shield without perforations covering a heated sensing element, the heated gas sensor positioned downstream of an engine throttle and upstream of the cylinder; and
   igniting the fuel vapors in the intake manifold gas flow in a vicinity of the heated sensing element of the heated gas sensor, retarding flame propagation of the ignition by the shield, and retaining the flame propagation within the shield, the flame propagation being retarded while still allowing gas to permeate the shield so that measurement of the intake manifold oxygen concentration is carried out.

13. The method of claim 12, further comprising generating the measurement in response to an operating temperature of the gas sensor being between 700 and 850° C.

14. The method of claim 13, wherein the fuel is gasoline.

15. The method of claim 14, wherein an amount of fuel delivered to the engine is based on the measurement of the intake manifold oxygen concentration generated by the gas sensor in the intake manifold.

16. The method of claim 14 wherein the fuel vapors pass through the porous metal shield without perforations and interact with the heated sensing element to ignite.

* * * * *